United States Patent [19]

Goldgaber et al.

[11] Patent Number: 5,744,368

[45] Date of Patent: Apr. 28, 1998

[54] METHODS FOR THE DETECTION OF SOLUBLE AMYLOID β-PROTEIN (βAP) OR SOLUBLE TRANSTHYRETIN (TTR)

[75] Inventors: Dmitry Y. Goldgaber, Setauket; Alexander L. Schwarzman, St. James; Moisés Eisenberg-Grünberg, Port Jefferson Station, all of N.Y.

[73] Assignee: Research Foundation of State University of New York, Albany, N.Y.

[21] Appl. No.: 148,117

[22] Filed: Nov. 4, 1993

[51] Int. Cl.$^6$ .................. G01N 33/566; G01N 33/53
[52] U.S. Cl. .................. 436/501; 435/7.8; 436/503; 436/504; 436/518; 436/804
[58] Field of Search .................. 436/501, 504, 436/503, 518, 528, 531, 804; 435/7.93, 7.8, 7.9

[56] References Cited

U.S. PATENT DOCUMENTS

| | | | |
|---|---|---|---|
| 4,666,829 | 5/1987 | Glenner et al. | 435/6 |
| 4,816,388 | 3/1989 | Sipe et al. | 435/6 |
| 5,137,873 | 8/1992 | Yankner | 514/15 |
| 5,164,295 | 11/1992 | Kisilevsky et al. | 435/7.8 |

FOREIGN PATENT DOCUMENTS

9012871   1/1990   WIPO.

OTHER PUBLICATIONS

Costa et al., Scand. J. Immunol. 38:177–182 (1993) "Immunoassay for Transthyretin Variants Associated With Amyloid Neuropathy".

Thylen et al., The Embo Journal, vol. 12, No. 2:743–748 (1993) "Modifications of Transthyretin in Amyloid Fibrils:Analysis of Amyloid from Homozygous and Heterozygous Individuals with the Met30 Mutation".

Elovaara et al., Acta Neurol Scand. 74:245–250 (1986) "Serum Amyloid A Protein, Albumin and Prealbumin in Alzheimer's Disease and in Demented Patients With Down's Sydrome".

Kanemaru et al., American Journal of Pathology, vol. 137, No. 3, (1990) "The Presence of a Novel Protein in Calf Serum that Recognizes β Amyloid in the Formalin-fixed Section".

Schwartzman et al., Society for Neuroscience, Abstracts, vol. 19, Part 1 (23rd Annual Meeting, Washington, D.C. Nov. 7–12, 1993) "Sequestration of Amyloid β Protein".

Gregori et al., Society for Neuroscience, Abstracts, vol. 19, Part 1 (23rd Annual Meeting, Washington, D.C. Nov. 7–12, 1993) "Extracellular, But Not Intracellular Form of Amyloid Beta–Protein Precursor Can Be Degraded Through The Ubiquitin Pathway".

Shirahama et al., American Journal of Pathology, (1982), "Senile Cerebral Amyloid Prealbumin as a Common Constituent in the Neuritic Plaque, in the Neurofibrillary Tangle, and in the Microangiopathic Lesion".

Blake et al., J. Mol. Biol. 121:339–356 (1978) "Structure of Prealbumin: Secondary, Tertiary and Quaternary Interactions Determined by Fourier Refinement at 1.8 Å".

Strittmatter et al., Experimental Neurology 122:327–334 (1993) "Avid Binding of βA Amyloid Peptide to its Own Precursor".

Murrell et al., J. Biol. Chem. 267 (23):16595–600 (1992) "Production and Functional Analysis of Normal and Variant Recombinant Human Transthyretin Proteins".

Uemichi et al., J. Med. Genet 29 (12):888–91 (1992) "A New Mutant Transthyretin (Arg 10) Associated With Familial Amyloid Polyneuropathy".

Strittmatter et al., Proc. Natl. Acad. Sci. USA, 90:1977–1981 (1993) "Apolipoprotein E: High–avidity Binding to β–Amyloid and Increased Frequency of Type 4 Allele in Late–Onset Familial Alzheimer Disease".

Jacobson et al., VII International Symposium on Amyloidosis—Final Program—Queen's University (Kingston, Ontario, Canada) Jul. 11–15, 1993 "Transthyretin Ser 6 Gene Frequency In Individuals Without Anyloidosis".

Riisoen H, Acta Neurol Scand (Denmark) Dec. 1988, 78(6) p. 455–9. "Reduced Brealbumin (Transthyretin) in CSF of severely demented patients with Alzheimers's Disease".

Wide, L, Non Competitive and Competitive Binding Assays In: Principles of Competitive Protein–Binding Assays Second Edition ©1983 John Wiley & Sons NY pp. 243–254.

*Primary Examiner*—Donald E. Adams
*Assistant Examiner*—Patricia A. Duffy
*Attorney, Agent, or Firm*—Morgan & Finnegan, L.L.P.

[57] ABSTRACT

This invention is directed to methods and compositions for preventing aggregation of amyloid β-protein (βAP) aggregation. Aggregation of amyloid β-protein is associated with the deposition of amyloid in the brain. Amyloid β-protein-binding compounds such as transthyretin are described which form complexes with βAP and prevent formation of amyloid. This invention also identifies the serine 6 mutation in the TTR gene as predictive of person at risk for developing βAP associated amyloidosis.

9 Claims, 8 Drawing Sheets
(1 of 8 Drawings in Color)

FIG. 1A
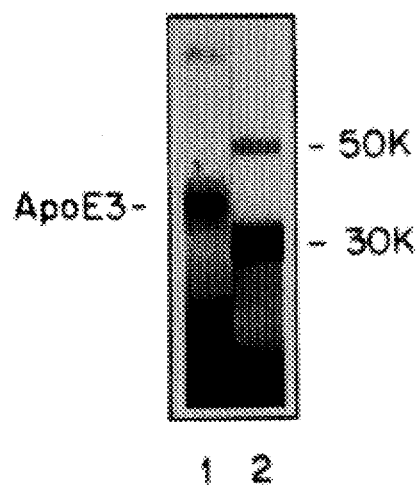
FIG. 1B
FIG. 1C
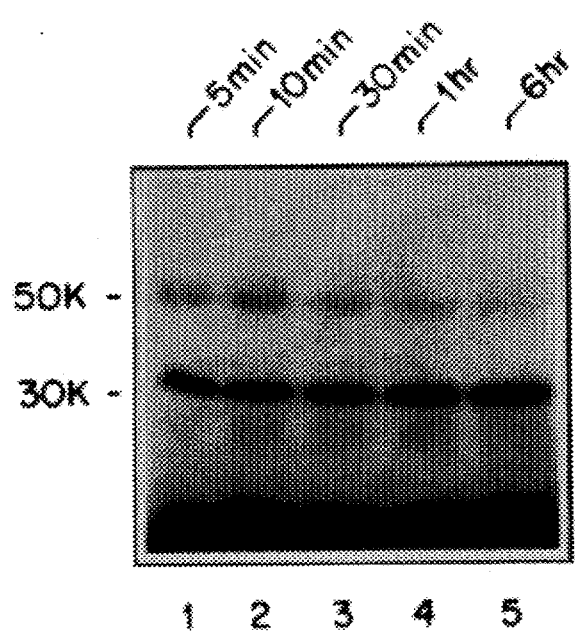
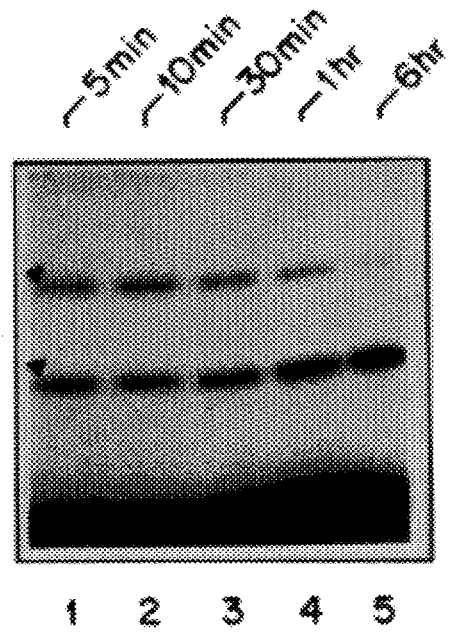

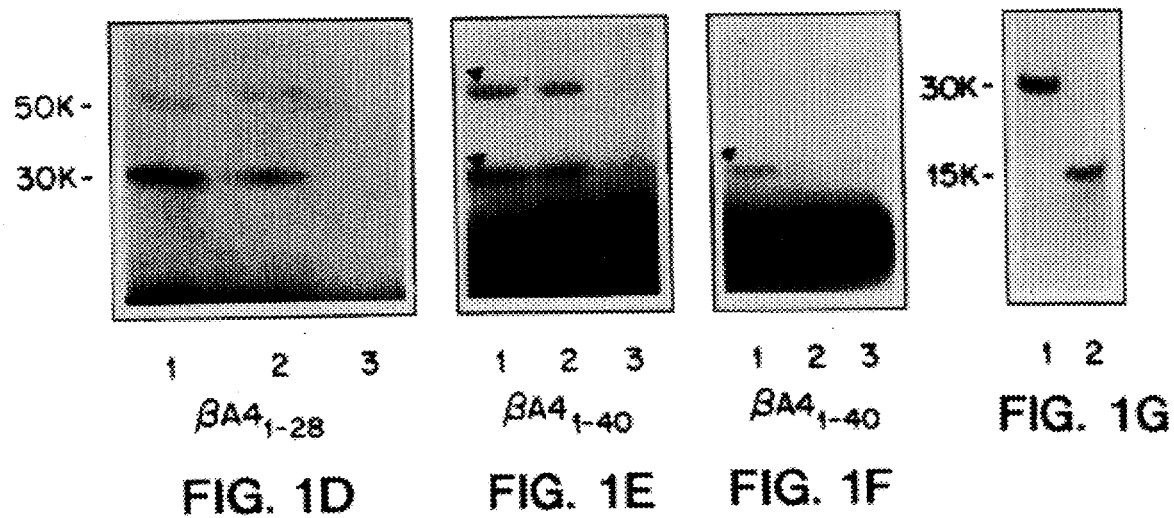

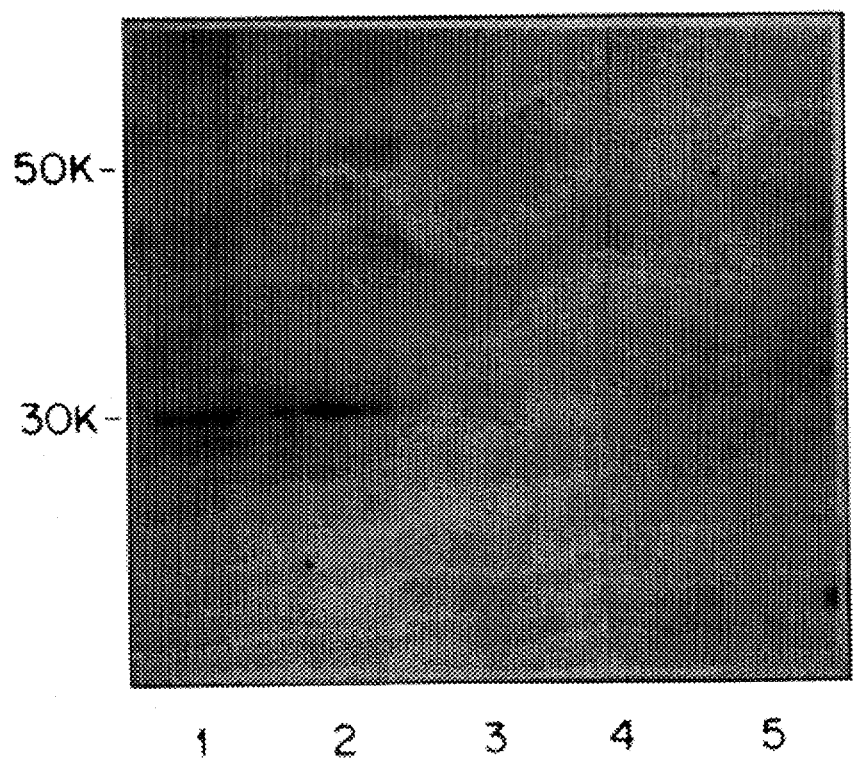
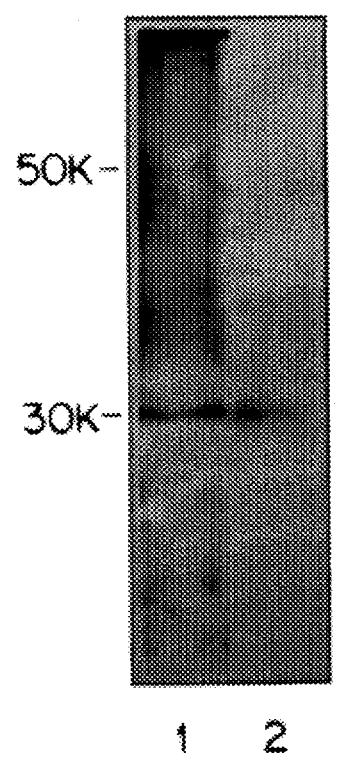
FIG. 3A
FIG. 3B

FIG. 4A
FIG. 4B
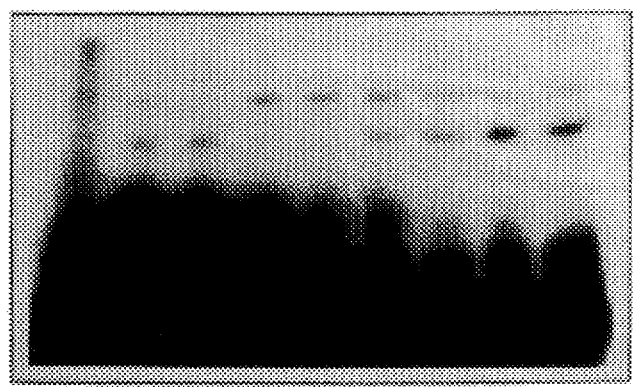
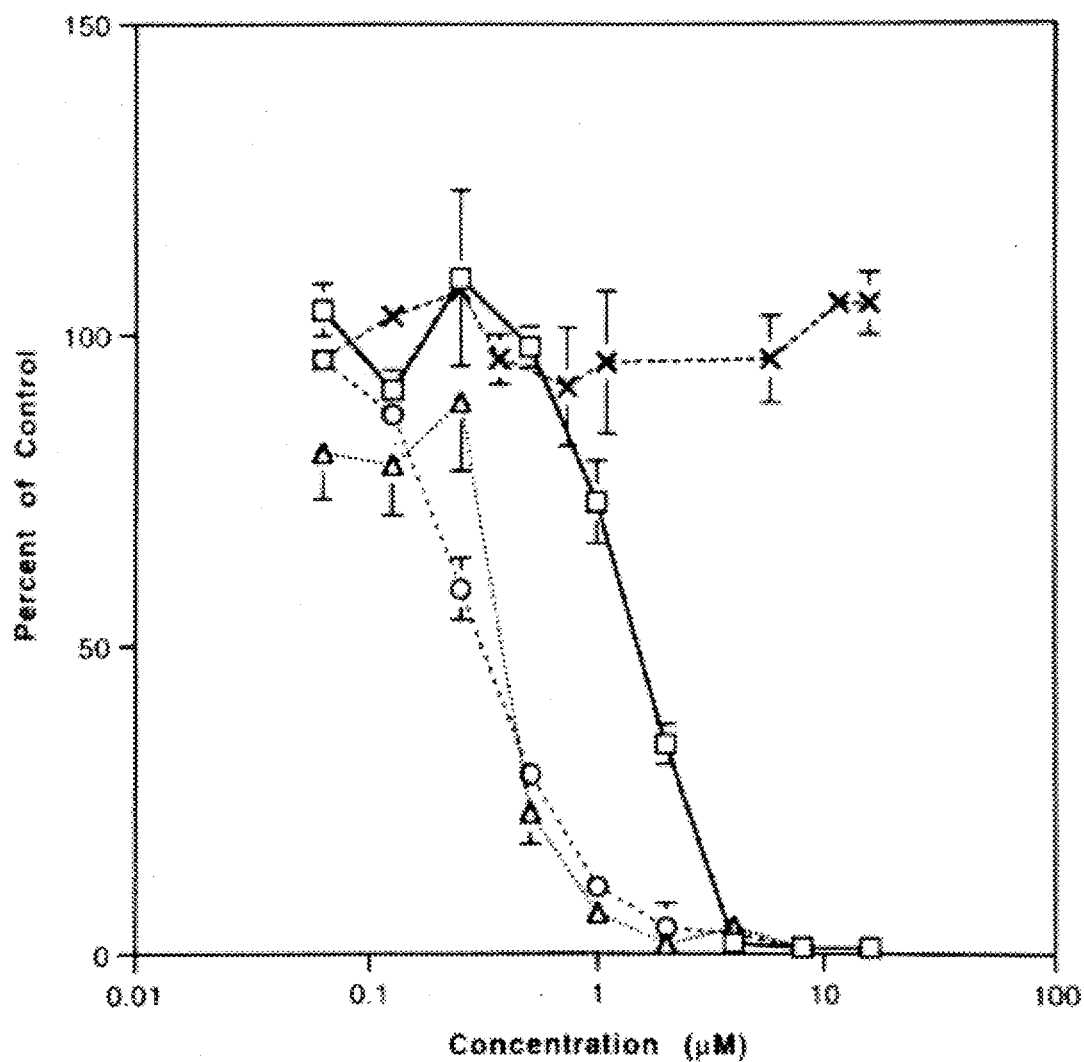
FIG. 4C

METHODS FOR THE DETECTION OF SOLUBLE AMYLOID β-PROTEIN (βAP) OR SOLUBLE TRANSTHYRETIN (TTR)

This invention was made with Government support under Grant NIA 5 R01 AG0932004 awarded by the National Institute of Health. The Government has certain rights in the invention.

TECHNICAL FIELD OF THE INVENTION

This invention relates to methods and compositions useful for preventing aggregation of amyloid β-protein. Aggregation of amyloid β-protein is associated with development of amyloid deposits which are formed in persons with various forms of dementia. This invention also relates to the identification of a genetic marker useful for identifying persons at risk for developing amyloidosis. Accordingly, this invention relates to methods of diagnosing, preventing and treating amyloidosis associated with aggregation of amyloid β-protein.

BACKGROUND OF THE INVENTION

The cardinal pathological feature of Alzheimer's disease is the formation of amyloid depositions of aggregated amyloid β-protein (βAP) in the brain and cerebralvasculature. Amyloidosis is a pathologic condition characterized by the deposition of amyloid, a generic term describing abnormal extracellular and/or intracellular deposits of fibrillar proteins. Amyloid deposits may be formed in a variety of tissue and organs including brain, liver, heart, kidney, etc. Advanced amyloidosis may cause extensive tissue breakdown.

Proteins involved in the formation of amyloid have the following common properties: 1) they possess a β-pleated sheet secondary structure; 2) they form insoluble aggregates; 3) they exhibit green birefringence after Congo red staining; and 4) they possess a characteristic fibrillar structure when observed under an electron microscopic. Proteins which have been identified as capable of forming amyloid in human disease include: immunoglobulin light chains, protein AA, $\beta_2$-microglobulin, transthyretin, cystatin C variant, gelsolin, procalcitonin, protease resistant protein $PrP^{scr}$, and amyloid β-protein.

Amyloid β-protein, or βAP, a polypeptide of 39 to 43 amino acids is a 4-kilodalton derivative of a large transmembrane glycoprotein amyloid β precursor protein (APP). See, D. L. Price, D. R. Borchelt and S. S. Sisodia, Proc. Natl. Acad. Sci. U.S.A. 90, 6381 (1993); Selkoe, D. J. "Amyloid Protein and Alzheimer's Disease", Scientific American, (1991) 265:68 for review. The sequence of amyloid β-protein was determined by Glenner and Wong, Biochem. Biophys. Res. Comm. (1984) (120:885) and U.S. Pat. No. 4,666,829 which is incorporated herein by reference. βAP is found in an aggregated, poorly soluble form, in extracellular amyloid depositions in brains and leptomeninges of patients with Alzheimer's disease (AD), Down syndrome (DS), and hereditary cerebral hemorrhage with amyloidosis—Dutch type (HCHWA-D) (D. J. Selkoe, Neuron 6, 487 (1991); D. L. Price, D. R. Borchelt and S. S. Sisodia, Proc. Natl. Acad. Sci. U.S.A. 90, 6381 (1993)). In contrast, βAP has been detected in a soluble form in cerebral spinal fluid (CSF) and plasma of healthy individuals and patients with AD. Seubert, P. et al. Nature (1992), 359:325.

A number of studies of synthetic βAP in vitro have shown that βAP aggregates easily and forms amyloid fibrils similar to the fibrils found in brains of patients with AD and DS (E. M. Castano et al., Biochem. Biophys. Res. Commun. 141, 782 (1986); D. Burdick et al., J. Biol. Chem. 267, 546 (1992); J. T. Jarrett and P. T. Lansbury, Jr., Cell, 73, 1055 (1993)). The mechanism by which this normally produced peptide forms amyloid is unknown. It has also been unknown why βAP, in a soluble form, is present in biological fluids of healthy individuals and patients with AD.

Recently, several extracellular proteins have been identified that bind immobilized βAP. These include apoE, apoJ, and APP, all of which are found in CSF (W. J. Strittmatter et al., Proc. Natl. Acad. Sci. U.S.A. 90, 8098 (1993); J. Ghiso et al., Biochem. J. 293, 27 (1993); W. J. Strittmatter et al., Experimental Neurology 122, 327 (1993)). The binding of apoE, the major CSF apoliproprotein which exists in 3 major isoforms, is particularly relevant to late-onset familial and sporadic AD. Patients homozygous for the apoE4 isoform have more amyloid depositions than patients homozygous for the apoE3 isoform (W. J. Strittmatter et al., Proc. Natl. Acad. Sci. U.S.A. (1993), 90:1977). The inheritance of the APOE4 allele also significantly increases the risk and decreases the age of onset of AD (E. H. Corder et al., Science 261, 921 (1993)). Although, apoE appears to be a candidate for sequestration of βAP, it was unknown as to whether apoE bound βAP and formed complexes in vivo.

Transthyretin (TTR), also referred to as prealbumin, is a homotetrameric, protein each subunit of which contains 127 amino acids. Its secondary, tertiary and quartenary structure has been described Blake et al. in J. Mol. Biol. (1978) 121:339, which is incorporated herein by reference. The TTR tetramer has a molecular weight of about 54,980 daltons. TTR is synthesized in liver and the chorioid plexus and is present in the serum and cerebral spinal fluid (CSF). In human CSF, TTR is usually present at a concentration of about 0.3 micromolar. Only albumin which is present in a concentration of about 2 micromolar is present in CSF at a higher concentration. TTR is known to be the main carrier of thyroxin and vitamin A across the blood brain barrier. The presence of TTR in amyloid deposits associated with AD and Down's syndrome has been suggested by Shirahama, T. et al. Am. J. Pathol. (1982), 107:041, but not confirmed. Eikelenboom, P. and F. C. Stam, Virchows Arch. [Cell P.] (1984), 47:17.

TTR which forms amyloid deposits in patients with certain familial amyloid polyneuropathy's (FAP's) has been determined to have various amino acid substitutions compared to circulating transthyretin of normal individuals. For example, a substitution of a methionine for valine at amino acid residue number 30 has been identified in kinships of Portuguese (Saraiva, M. J. M. et al., J. Clin. Invest (1984) 74:104), Japanese (Tawara, S. et al., Biochem. Biophys. Res. Comm. (1983) 116:880) and Swedish ancestry (Dwulet, et al., Proc Natl. Acad. Sci. U.S.A. (1984) 81:694; and Whitehead, A. S. et al., Mol. Biol. Med. (1985) Vol. 7). In another form of FAP disease, the TTR protein present in the affected individuals has serine substituted for isoleucine at position 84. Wallace et al., Clin. Res. (1985) (33:592A). Studies of TTR levels in AD patients and patients with Down syndrome report that TTR concentrations may be decreased in these patients. Riisoen, H., Acta Neurol. Scand. (1988) 78:455 and Elovaara, I. et al., Acta Neurol. Scand. (1986) 74:245.

Sipe et al., U.S. Pat. No. 4,186,388 refers to the cloning of the human TTR gene and its use to identify various forms of FAP's. Use of the gene and specific cDNA fragments capable of hybridizing with DNA fragments of biological samples is reported to be useful to identify individuals with various forms of FAP disease including type I FAP disease in which methionine is substituted for valine at position 30 as described above. Sipe et al. report that TTR is associated with amyloid deposits in Alzheimers disease, FAP, and senile cardiac amyloidosis. Sipe et al., further state that the function of TTR in the nervous system is unknown.

Chromosomal localization of genes causing AD can facilitate early diagnosis of persons with this disease. Prenatal diagnosis in affected families is also possible once a genetic marker for a disease is identified. Subsequent delineation of closely linked markers which show strong linkage disequilibrium with the disorder and ultimately, identification of the defective gene can allow screening of the entire at-risk population to identify carriers, begin early prophylactic or therapeutic invention if available and potentially reduce the incidence of new cases.

There is a need for effective methods and compositions for preventing aggregation of βAP and of identifying individuals at risk for developing amyloidosis.

SUMMARY OF THE INVENTION

This invention provides methods and compositions useful for preventing aggregation of amyloid β-protein. The methods are useful for preventing aggregation of amyloid β-protein (βAP) in vivo and in vitro and therefore, may be used to prevent or treat mammals, especially humans with amyloidosis associated with βAP aggregation. The methods are also useful for diagnosing persons at risk for developing amyloidosis associated with amyloid β-protein aggregation.

The compositions of this invention promote complex formation between βAP and βAP-binding compounds such as TTR, which are capable of complexing with βAP, in a manner which prevents βAP from self-aggregating and forming amyloid.

The method of preventing aggregation of βAP according to this invention comprises providing a βAP-binding compound to a fluid or biological tissue comprising βAP. The βAP-bind compound is provided in an amount sufficient to sequester βAP in complexes comprising βAP and the βAP-binding compound so that βAP is not available to self-aggregate.

By preventing βAP aggregation and amyloid deposition, this invention also provides methods and compositions useful for preventing and treating diseases associated with βAP amyloid formation, including, for example, AD, Down's Syndrome and hereditary cerebral hemorrhage with amyloidosis—Dutch type.

This invention also provides assays for detecting βAP or TTR in a biological fluid based on the formation of complexes comprising βAP and at least one βAP-binding compound.

Also provided is a method of detecting persons at risk for developing βAP associated amyloidosis by identifying the presence of a mutation in the TTR gene. The mutation involves a G-A transition in codon 6 resulting in the substitution of serine at amino acid position 6 for the normally present glycine. Because this mutation also creates a BsrI restriction site, this invention also provides a method of identifying persons at risk for developing βAP amyloidosis. The method comprises obtaining DNA from a person; amplifying the gene, or portion thereof, comprising the codon for the sixth amino acid (glycine) of TTR; digesting the amplified DNA with a restriction enzyme such as BsrI; and analyzing the fragments for the presence of an alteration in restriction fragments compared to controls to detect the Serine 6 mutation.

It is an object to this invention to provide methods of preventing aggregation of βAP in solution by sequestering βAP in complexes with βAP-binding compounds such as TTR. Prevention of aggregation is useful for preventing fibril and amyloid formation associated with disease.

Another object of this invention is to provide compositions useful for complexing with βAP to so as to sequester βAP preventing βAP from forming aggregates.

It is another object to this invention to provide assays suitable for determining the amount of βAP or TTR in a biological fluid.

Another object of this invention is to provide methods and compositions useful for genetic screening of individuals to identify individuals who have a mutation in the TTR gene and who may be at risk for developing βAP associated amyloidosis.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 1a–1g are analysis of $^{125}$I-β complexes with CSF proteins. 10 μl CSF were incubated with $10^5$ dpm $^{125}$I-βAP$_{1-28}$ (specific activity 3–6×$10^6$ dpm/μg) in a final volume of 20 μl PBS, Ph 7.4 at 37° C. for 8 hours, except an experiment illustrated in FIG. 1a. The complexes were analyzed by electrophoresis in a 12% SDS-polyacrylamide gel under non-reducing conditions except for an experiment illustrated in FIG. 1g, lane 2.

Figure 2A:
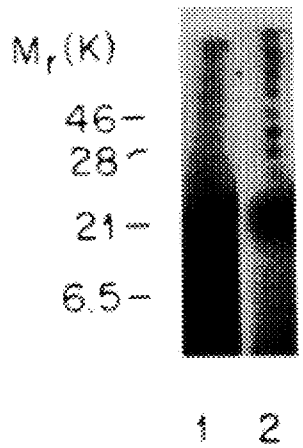

1a. Comparison of complexes of $^{125}$I-Aβ$_{1-28}$ with ApoE3 (1.5 μM) (lane 1) and with CSF proteins (lane 2) formed after incubation at 37° C. for 24 hours.

1b. Time course of complex formation of $^{125}$I-Aβ$_{1-28}$ with CSF proteins.

1c. Time course of complex formation of $^{125}$I-Aβ$_{1-28}$ with CSF proteins in presence of 1.5 μM human plasma ApoE3.

1d. Competition of complex formation of $^{125}$I-Aβ$_{1-28}$ with CSF proteins by unlabeled Aβ$_{1-28}$.

CSF (lane 1), CSF plus 10 fold excess of unlabeled Aβ$_{1-28}$ (lane 2), CSF plus 200 fold excess of unlabeled Aβ$_{1-28}$.

1e. Competition of complex formation of $^{125}$I-Aβ$_{1-40}$ with CSF proteins by unlabeled Aβ$_{1-40}$.

CSF (lane 1), CSF plus 10 fold excess of unlabeled Aβ$_{1-40}$ (lane 2), CSF plus 200 fold excess of unlabeled Aβ$_{1-40}$.

1f. Competition of complex formation of $^{125}$I-Aβ$_{1-40}$ with TTR by unlabeled Aβ$_{21-40}$.

0.1 μM TTR (lane 1), 0.1 μM TTR plus 100 fold excess of unlabeled Aβ$_{1-40}$ (lane 2), 0.1 μM TTR plus 500 fold excess of unlabeled Aβ$_{1-40}$ (lane 3).

1g. Analysis of complexes of $^{125}$I-Aβ$_{1-28}$ with TTR under different conditions. Before electrophoresis the samples were incubated in 100 mM Tris-HCl, pH 6.8 without β-mercaptoethanol for 5 minutes at room temperature (lane 1), or were boiled for 10 minutes in a complete Laemli buffer with 0.2M β-mercaptoethanol (lane 2).

Figure 2B:
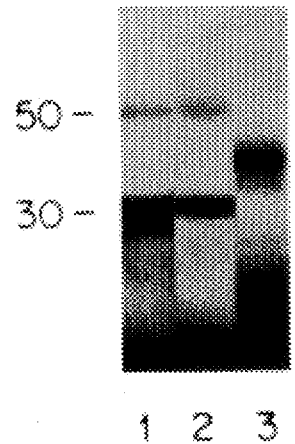

FIGS. 2a and 2b are analysis of $^{125}$I-βAP complexes with CSF proteins.

2a. SDS-PAGE analysis of $^{125}$I-βAP$_{1-28}$ incubated for 24 hrs. in PBS (lane 1) and after centrifugation through a 20% sucrose cushion at 15000×g for 10 minutes (lane 2).

2b. SDS-PAGE analysis complexes of $^{125}$I-βAP$_{1-28}$ with CSF proteins formed after incubation for 24 hrs. (lane 1) or 10 minutes (lane 2); or after incubation with human apoE3 in PBS after 24 hrs. (lane 3).

FIGS. 3a and 3b are western blot analysis of TTR-βAP complexes.

3a. βAP$_{1-40}$ (10 μg) incubated overnight at 37° C. in PBS, pH 7.2 with CSF (10 μl, lane 1); TTR (1 μg, lane 2); BSA (50 μg, lane 3). Control consisted of CSF (10 μl, lane 4) and TTR (1 μg, lane 5) without βAP. Samples were analyzed by SDS-PAGE and immunoblotting with rabbit anti-βAP antibody SGY2134.

3b. Immunoblotting with rabbit anti-βAP antibody (SGY2134, lane 1) and sheep anti-TTR (lane 2) of βAP$_{128}$ and CSF (10 μl) overnight incubation in PBS, pH 7.2 at 37° C. analyzed by SDS-PAGE and immunoblotting. The immunoblot was cut lengthwise in two strip for analysis in lanes 1 and 2.

FIGS. 4a–4c show prevention of aggregation of βAP.

4a. $^{125}$I-βAP aggregates.

4b. Effect of TTR on aggregation of $^{125}$I-βAP.

4c. Thioflavin T based fluorometric assay of βAP$_{128}$ aggregation in the presence of different concentrations of borine serum albumin (×), TTR (□), apoE3 (△), and apoE4 (○). Each point represents the average of quadruplicate measurements and are plotted as percentages with standard error for the given concentrations.

Figure 5A:
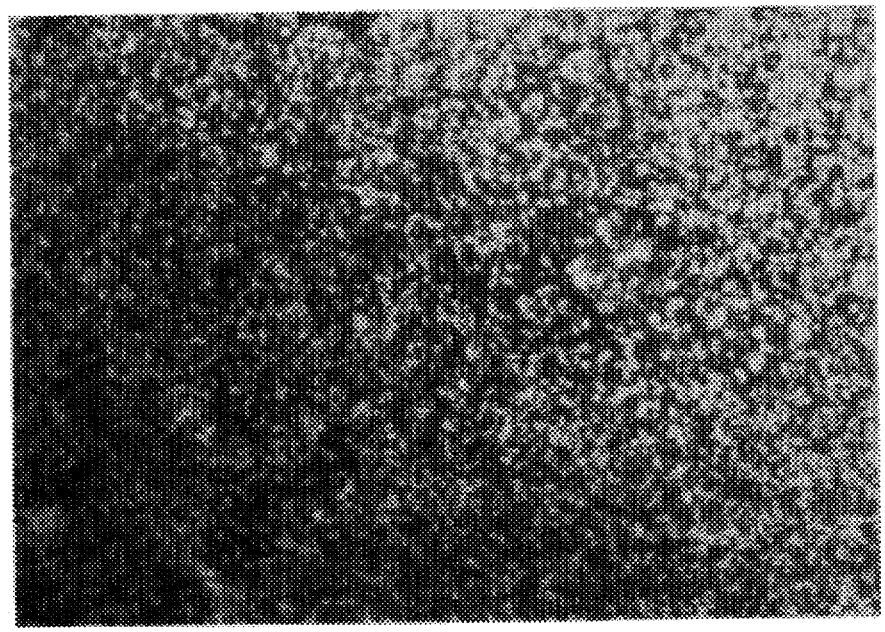
Figure 5B:
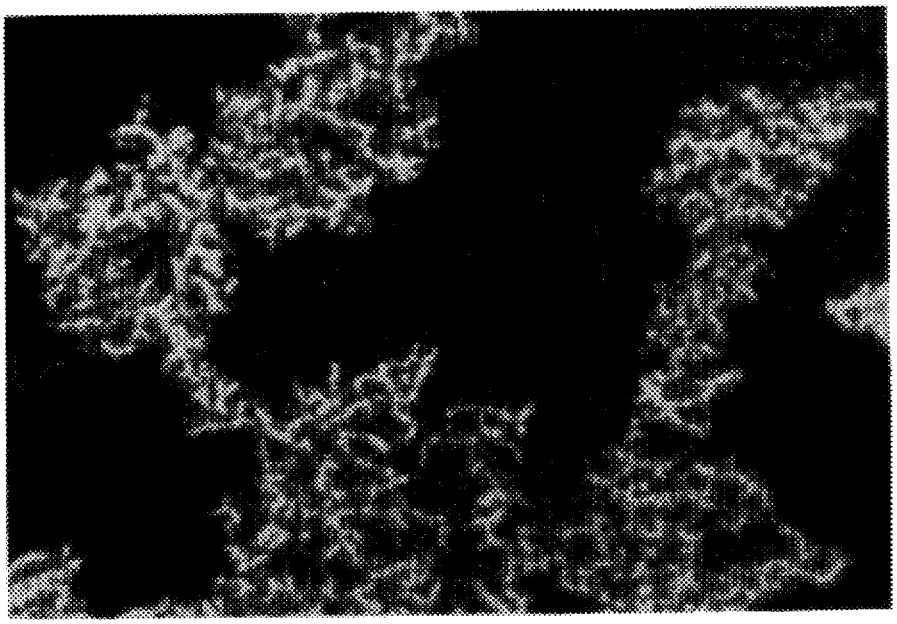

FIGS. 5a and 5b show congo red staining of βAP$_{128}$ aggregates in the presence of 5 μM BSA (5b) or 3 μM TTR (5a). Slides were viewed under polarized light at 200× magnification.

Figure 6A:
Figure 6B:
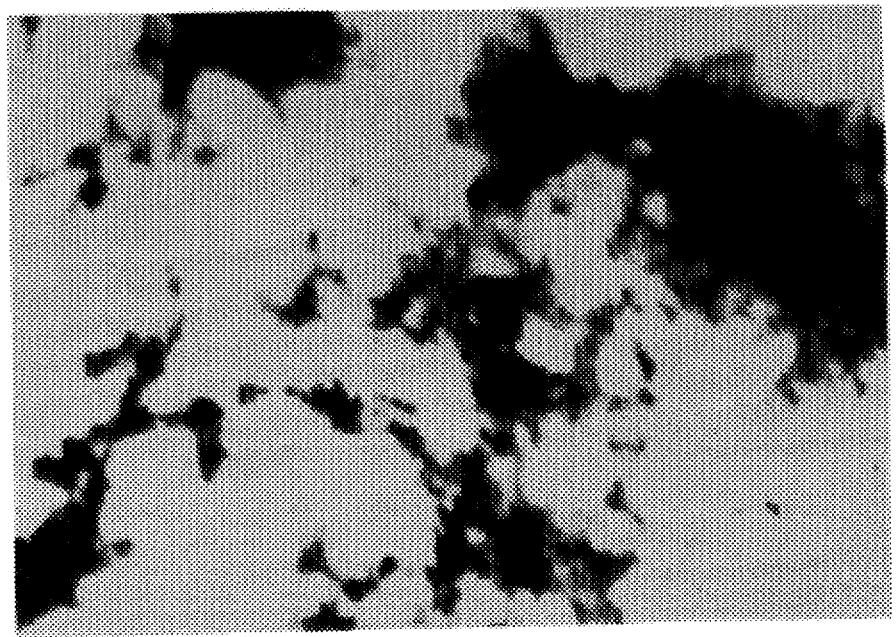

FIGS. 6a and 6b show an electron micrograph of βAP$_{128}$ aggregates without (6b) or with 2 μM TTR (6a). Scale bar, 100 nm. Samples were examined and photographed at magnification of 25,000 in a Hitachi-12 electron microscope.

Figure 7:
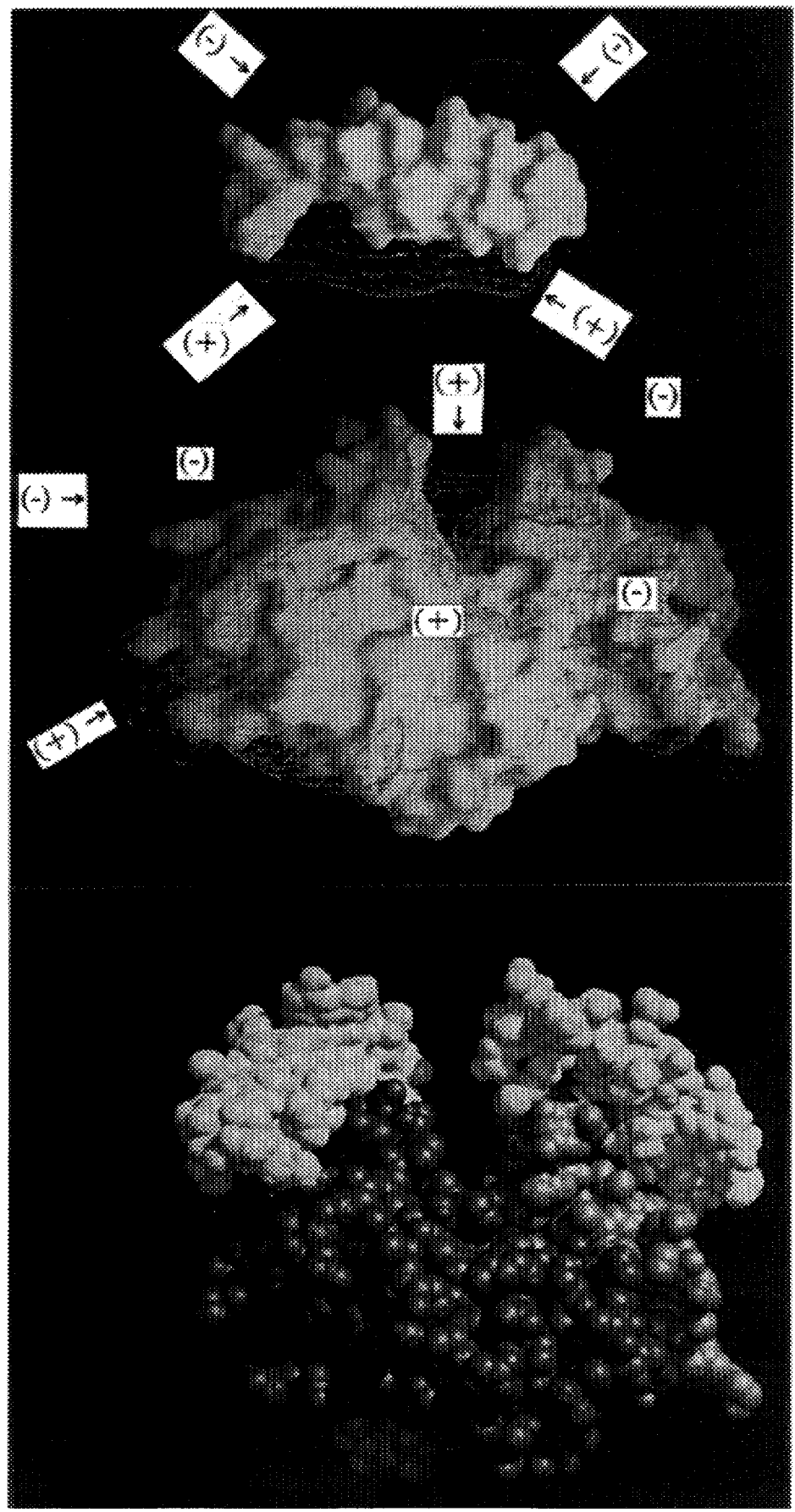

FIG. 7 shows computer graphic models of βAP (top), TTR dimer (middle) and TTR-βAP complex (bottom).

Figure 8:
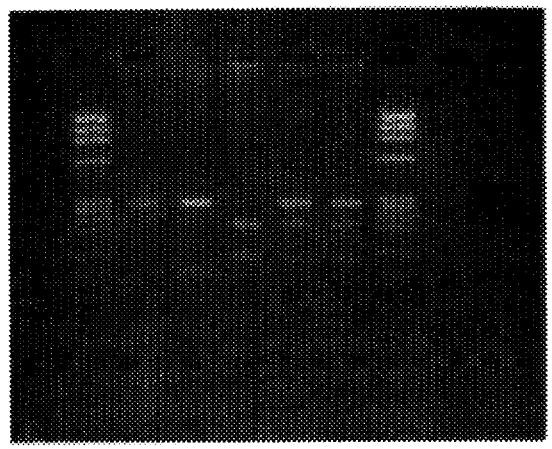

FIG. 8 shows serine 6 polymorphismin the TTR gene by agarose gel electrophoresis of a DNA fragment corresponding to exon 2 of TTR gene amplified by PCR and analyzed for the presence of the BsrI restriction site in individuals who are normal (lanes 2 and 3), homozygous (lane 4) and heterzygons (lanes 5 and 6) for the serine 6 mutation. Lanes 1 and 7 are Hae III digests of φ×174 DNA for use as molecular weight markers.

DETAILED DESCRIPTION OF THE INVENTION

This invention describes methods and compositions useful for preventing aggregation of soluble amyloid β-protein. We have determined that βAP present in cerebral spinal fluid (CSF) is predominantly bound to TTR. In addition, we have identified a unique binding interaction between TTR and βAP in biological fluids. In another embodiment of this invention a mutation in the gene encoding transthyretin has been identified in patients with AD, the presence of which is highly predictive of patients at risk for developing AD and is also useful for diagnosing persons with AD.

This invention provides compounds useful for preventing aggregation of βAP in solution. We have identified that βAP which normally self-aggregates when in solution, may be prevented from self-aggregating by causing the βAP to form a complex with βAP-binding compounds (BBC's). For the purposes of this invention, BBC's are any compound which form a complex with βAP and which prevent βAP aggregation and formation of amyloid. Examples of BBC's for use with this invention include, but are not limited to, TTR, TTR analogs, and apoE.

The identification of the ability of BBC's to prevent aggregation of βAP, and subsequent amyloid formation, provides for methods of diagnosing, preventing, and treating persons with, or at risk for developing amyloidosis resulting from βAP aggregation.

Binding of a BBC to βAP occurs at physiologically relevant concentrations. For example, TTR which is normally present in CSF at a concentration of about 300 nM may be caused to bind to βAP present in a solution at concentrations of about 3 nM, which is similar to βAP's concentration in CSF.

By assessing the binding interaction between a BBC, such as for example TTR, and βAP in an appropriate fluid or biological tissue including CSF, one can monitor the extent of BBC-βAP complex formation. Such monitoring of BBC-βAP complex formation may be done in the context of a diagnostic test to determine whether the normal BBC-βAP binding phenomenon is altered.

Alterations in BBC-βAP complex formation in vivo resulting from either alterations in BBC's or βAP may result in increased amounts of free βAP available to aggregate and form amyloid. Changes in the amino acid sequence of BBC's or βAP, or in their rate of synthesis or degradation may result in a decrease in complex formation resulting in βAP aggregation. Such alterations would put a person at risk for developing amyloid deposits resulting from βAP aggregation.

We have determined that TTR is the predominant BBC in CSF which is responsible for preventing βBAP from aggregating and forming amyloid. In CSF, TTR binds with βAP to form a complex which sequesters βAP and prevents βAP from self-aggregating. Because TTR is the predominant BBC in CSF, to determine if someone is at risk for developing amyloidosis resulting from βAP aggregation, it would be preferable to monitor the binding interaction between βAP and TTR. Binding of TTR to βAP may also be monitored to determine the effectiveness of a treatment directed at sequestering βAP or reducing the concentration of βAP available for aggregation. Measuring TTR-βAP binding interactions may also be used to identify other BBC's which are also suitable for complexing to βAP in a manner which sequesters βAP so that it is unavailable to aggregate and form amyloid depositions.

Binding of BBC to βAP may be measured by using standard binding assays known to those skilled in the art, based on the teachings disclosed herein. For example, βAP and TTR may be allowed to form complexes in solution. Detection of the complexes may be accomplished using chromatographic techniques, for example, molecular sieve exclusion chromatography. SDS-PAGE electrophoresis may also be used.

Assays involving immobilization of either βAP or TTR to a solid support may also be used to detect binding of the corresponding partner (i.e., TTR if βAP is immobilized). The method of Strittmatter, W. et al., *Proc. Natl. Acad. Sci., U.S.A.* (1993), 90:1977 which is incorporated herein by reference, for binding apoliprotein (APOE) to βAP, may be used to demonstrate complex formation between TTR and βAP. Detection of bound TTR or βAP may be accomplished by methods well known in the art including use of enzymatic or radioactive labels.

Binding of human TTR to βAP is specific. Evidence of specific binding between TTR and βAP may be provided using a competition assay. In such an assay, either one of βAP or TTR is labelled in a binding assay as described above. An excess of unlabelled ligand of the same type which is labelled (i.e., excess of βAP if labelled βAP is used) is included in the reaction mixture to compete with and prevent binding of the labelled ligand. Preferably, the unlabelled ligand will be present in the reaction mixture in excess of between 100 to 1000 times the concentration of the labelled ligand.

BBC's which are useful with this invention prevent the aggregation of βAP and subsequent amyloid formation. The inhibition by a BBC of one or more properties of amyloid, would be indicative of a BBC useful with this invention. These properties of amyloid include, for example, the ability of a BBC to 1) prevent βAP from assuming a β-sheet secondary structure, 2) prevent βAP from aggregating to form an insoluble structure, 3) inhibit βAP from forming structures which exhibit green birefringence after Congo red staining, and 4) prevent βAP from forming fibrils with typical electron microscopic appearance. TTR, which is a preferred BBC for use with this invention, prevents amyloid formation according to all four criteria.

We used computer modeling of the binding interaction between βAP and TTR to identify the specific molecular surfaces of βAP and TTR which participate in complex formation. The identification of the amino acid sequences of TTR and βAP relevant to the binding interaction allows for the synthesis of other BBC's including polypeptides, analogs of TTR and other molecules which would bind to βAP to prevent its aggregation. Analogs of TTR include fragments of TTR, and TTR having amino acid substitutions, deletions, or additions as well as other molecules that share a similar TTR binding domain which is important for preventing amyloid formation. The TTR analogs form complexes with βAP to prevent its aggregation and amyloid formation. In addition, unless otherwise specifically stated, reference herein to TTR is meant to include TTR analogs as well. Based on the teachings disclosed herein, other types of molecules may also be capable of binding to βAP to prevent its aggregation. Such molecules include organic molecules such as for example Buckministerfullerenes. Preferably, BBC's and TTR analogs bind to βAP at concentrations which avoid harmful side effects in an individual to whom they may be administered.

The TTR analogs may include analogs of TTR in which the amino acid sequence of human TTR is substituted with amino acids which allow for the TTR-βAP binding interaction to occur. Such substitutions include substituting neutral amino acids such as glycine, alanine, valine, leucine and isoleucine for other neutral amino acids present in the TTR sequence. In addition, substitution of aromatic amino acids present in TTR may be accomplished using phenylalanine, tyrosine or tryptophan. Aliphatic amino acids in TTR possessing hydroxyl groups may be substituted with serine or threonine. Amino acids present in TTR having basic side chains may be substituted with lysine, arginine, and histidine, whereas amino acids having acidic side chains may be substituted with aspartic acid or glutamic acid. Asparagine may be substituted for glutamine which both have amide chains.

Because of a large contact surface between βAP and TTR it may be possible that not all amino acid substitutions be a precise one-to-one equivalency. Some flexibility of the choices may be necessary, as long as the analog attempts to reproduce with reasonable fidelity the shape of the TTR binding surface and the engendered electrostatic potential mimics that of TTR within a reasonable range. More precisely the −1 kT electrostatic potential contour of the analog should cover essentially the same area as in TTR and its location should not be closer than about a 2 Å displacement toward the surface, as compared with the TTR potential contour.

Without being bound by theory, the portion of the amino acid sequence of TTR which participates in the binding with βAP extends from about amino acid residue 30 to 70. Within this amino acid sequence, the specific amino acids of TTR comprising Arg (34, 161), Ala (37, 164), Asp (38, 165), Thr (40, 167), Glu (42, 169), Glu, (62, 189), Val (65, 192), and Glu (66, 193) are preferred. (The first number is the order number at the first residue on chains 1 and 3; the second number refers to the residue in chains 3 and 4.)

According to the model, negative amino acid residues Asp (38, 165), Glu (42, 169), Glu (62, 189), and Glu (66, 193) present on the essentially convex surface of TTR comprising by all the amino acids specified in the preceding paragraph are responsible for generating a negative electrostatic potential around that specific region of TTR so as to specifically interact with the positive electrostatic potential engendered by specific positive amino acids on the surface of the βAP. These positive amino acids of βAP, which are located in an essentially concave surface which specifically interacts with TTR to form the complex include Arg (5), His (13), Lys (16), and Lys (28). These positive amino acids on βAP reside in the essentially concave larger contacting surface of βAP referred to above comprising amino acid residues Arg (5), Ser (8), Gly (9), Val (12), His (1 3), Gln (15), Lys (16), Phe (19), Phe (20), Asp (23), Val (24), Asn (27), and Lys (28).

The most important parameters for describing the binding interaction between TTR and βAP are the detailed curvatures of the surface and the electrostatic potentials generated by the charged amino acids. The contacting surfaces of TTR and βAP are the surfaces described by the listing of the specific amino acid residues in TTR and βAP listed above. The negative electrostatic potential on TTR is engendered by the negative amino acids listed above, and similarly, the positive amino acids on βAP engender the positive potential around its surface.

This invention includes other BBC's which bind to the TTR binding site of βAP, or portions thereof, and which prevent the aggregation of βAP and formation of amyloid. In addition, compounds which alter the TTR binding site of βAP, whether or not they bind to this site, but bind to βAP and prevent its aggregation are contemplated as well. Also, compounds that possess a surface shape and electrical change similar to the binding site of TTR or part thereof, could prevent βAP aggregation and amyloid formation and are contemplated as well.

This invention provides a method of preventing aggregation of soluble βAP present in a solution at a given concentration. βAP may be present in solutions in vitro or in vivo. Biological tissues in which βAP is present include CSF, cerebralvasculature, or brain. To prevent aggregation of βAP, a sufficient amount of TTR or TTR analog is provided to the βAP containing solution or tissue to form TTR-βAP complexes. As shown in FIG. 6, evidence of inhibition of aggregation may be demonstrated by the inhibition of βAP-fibril formation.

Inhibition of βAP may be accomplished over a wide BBC to βAP ratio. In CSF of normal individuals in which βAP is not aggregated, TTR is present at a concentration of about 300 nM, whereas βAP is present at about only 3 nM. Accordingly, a suitable ratio of TTR to βAP for use with this invention is about 100 to 1. However, in vitro, we have determined that TTR, at about 1.2 μM, prevents about 50% of aggregation of βAP present at about 300 μM. FIG. 4. Therefore, a ratio of BBC to βAP of about 1 to 100 is also preferred for use with this invention. In addition, a ratio of BBC to βAP of about 1 to 4 is also preferred based on the stoichiometry of the βAP and TTR binding. BBC to βAP ratios of 1 to 2 and 1 to 1 are also preferred. These ratios may be optimized for use with BBC's besides TTR.

As the concentration of TTR is increased, the formation of βAP aggregates having a high molecular weight decreases. FIG. 4(b). Because as little as about 3 μM TTR can essentially completely inhibit aggregate formation of about 300 μM βAP, it is likely that TTR also inhibits aggregation of βAP by mechanisms other than by the simple stoichiometric model discussed above. Accordingly, the administration of BBC's such as TTR would be useful to prevent the enlargement of amyloid deposits existing prior to initiation of treatment.

Endogenous TTR present in vitro or in vivo, which is capable of binding to βAP at the TTR binding site in a manner which prevents βAP aggregation, for the purpose of this invention is considered to contribute to the total amount of TTR or TTR analog in determining the ratios described above. In situations were endogenous TTR is mutated or is in a form which does not effectively prevent βAP aggregation, then the amount of exogenous TTR, or TTR analog, added to the solution would be an amount sufficient to inhibit βAP aggregation independent of the endogenous TTR and preferably would be an amount to achieve one of the ratios described above.

The TTR-βAP binding interaction described according to the invention is also useful in assays to determine the amount of βAP or TTR in a biological sample. Several protocols known in the art including immunoassay and receptor binding assays may be adapted to take advantage of the complex formation formed between βAP and TTR. For example, according to one embodiment of this invention, an assay to determine the amount of soluble βAP present in a sample would comprise the steps of combining the sample with a soluble or bound BBC, such as TTR, in the presence of a known amount of soluble labelled βAP and detecting the amount of βAP in the sample. According to a preferred embodiment, TTR is bound to a solid support.

In another embodiment of the assay, a sample containing an unknown amount of TTR or mutated form of TTR may be combined with βAP bound to a solid support. Labeled TTR may then be added to the sample to determine by competition the amount of endogenous TTR or mutated TTR present in the sample.

Other assay protocols including sandwich assays are contemplated by this invention. For example, to measure βAP in a sample, TTR may be linked to an insoluble support to which is added the sample containing the unknown amount of βAP. Anti-βAP-antibody which is labeled may then be added to the sample to detect the amount of bound βAP. Such an assay may also be constructed to determine the amount of TTR in a sample.

In another embodiment of the invention, soluble βAP in vivo is prevented from aggregating by providing a BBC to form complexes with βAP in vivo. The BBC, preferably TTR, is provided in an amount sufficient to complex with soluble βAP so as to reduce the concentration of free βAP in solution. Reduction of soluble βAP and the formation of BBC-βAP complexes sequesters the βAP and decreases the amount of βAP available for forming aggregates and amyloid deposition. Inhibition of βAP aggregation and amyloid formation is useful from the prevention or treatment of Alzheimer's Disease, Down's Syndrome and hereditary cerebral hemorrhage with amyloidosis—Dutch type.

The methods and compositions of this invention are also suitable for use with mammals besides humans such as monkeys, dogs and any other mammal that develops βAP amyloidosis. (D. J. Selkoe, Neuron 6, 487 (1991).

This invention also provides a method of identifying persons at risk for developing amyloidosis based on the identification of a mutation in the TTR gene involving a substitution of serine for glycine at position 6 of TTR. This substitution arises from a single point mutation in which the first guanine in the GGT codon is substituted with an adenine to produce the AGT codon. A study by Jacobsen et al. "Transthyretin ser 6 gene frequency in individuals without amyloidosis", *VII International Symposium on Amyloidosis*, Jul. 11–15, 1993, 100, which is incorporated herein by reference, reports that the serine 6 gene is a common normal TTR polymorphism present at a frequency of about 12% and, "apparently not associated with amyloidosis in the Caucasian population." We have surprisingly found that in a population of 55 unrelated AD patients, 10 (i.e. 18%) were heterozygous for this serine 6 mutation. As AD is believed to be a heterogenous disorder arising from a variety of causes, this result is consistent with the serine 6 mutation identifying a subpopulation of AD patients. This mutation was found in 7 families with patients with late onset of AD disease.

To identify persons at risk of developing AD associated with the serine 6 mutation, the DNA containing the second exon encoding TTR may be sequenced by methods known to those skilled in the art, or the DNA may be analyzed using restriction enzymes which can identify a change in the recognition site for the restriction enzyme. The substitution of A for G, destroys an MspI site and creates a BsrI site. The methods described in Sipe et al. U.S. Pat. No. 4,816,388, which is incorporated herein by reference, may also be modified to identify the serine 6 mutation.

In one method, PCR-SSCP analysis as described by Orita et al., *Genomic*, (1989), 5:874–879, which is incorporated herein by reference, is performed to identify the serine 6 mutation. Using PCR, primers which amplify the second exon of TTR may be used to amplify the region of the gene containing the serine 6 mutation. PCR may be performed using methods described in Mullis et al. U.S. Pat. No. 4,683,195, which is incorporated herein by reference. The following oligonucleotide probes are suitable for amplifying the appropriate region of exon 2 of TTR:

5' CGC TCC AGA TTT CTA ATA CCAC 3'(1515–1537) (SEQ ID NO:1)

5' AGT GAG GGG CAA ACG GGA AGAT 3' (1791–1769) (SEQ ID NO:2)

(The number in parenthesis represents the positions of the bases in the TTR gene.)

Following amplification of the gene fragment, the fragment may be sequenced or treated with restriction enzymes to determine whether the serine 6 mutation is present. Following separation of the amplified DNA fragment from the genomic DNA, the amplified fragment may be digested with BsrI to determine if this restriction site is present.

The identification of a marker associated with a form of AD lends itself to the formulation of kits which can be utilized in diagnosis. Such a kit may comprise a carrier being compartmentalized to receive in close confinement one or more containers wherein a first container may contain oliogonucleotides for amplifying the appropriate region of the genomic DNA. Other containers may contain reagents, such as restriction enzymes or labelled probes, useful in the detection of the mutation. Still other containers may contain buffers and the like.

BBC's such as TTR, and in particular, analogs suitable for use in this invention, may be produced by means known in the art including linking of individual amino acids to construct specific sequences, modification of purified TTR or by recombinant techniques. Recombinant production of TTR is described in Sipe et al., U.S. Pat. No. 4,816,388 which is incorporated herein by reference. To produce TTR analogs, cDNA encoding TTR may be modified to contain coding sequences coding for the desired TTR analog. Standard synthetic chemical techniques may be used for producing other BBC's.

To provide treatment, or prevent amyloidosis associated with βAP aggregation, BBC's such as TTR, should be administered to the individual in need of treatment in a therapeutically effective amount. Preferably, the BBC should be administered to the individual in an amount sufficient to achieve a concentration in vivo sufficient to prevent aggregation of βAP.

BBC's such as TTR, which are to be administered according to this invention may be administered as a pharmaceutical composition further comprising a biologically acceptable carrier including, but not limited to, saline, buffer, dextrose and water.

BBC's such as TTR may be administered by known methods including, sublingual, intravenous, intraperitoneal, percutaneous or intranasal modes of administration. Local administration directly to the site of action may also be desirable and may be accomplished through means known in the art including, but not limited to, injection, infusion and implantation of infusion devices containing the BBC. Similarly to administration of other peptides, administration is preferably by means which avoid contact with the gastrointestinal tract. The administration of a BBC such as TTR directly to the CSF may be accomplished by intrathecal injection. In a preferred method of the invention, BBC, and in particular TTR, is provided to the individual in need of treatment by inducing its endogenous production in the individual in need of treatment.

In another embodiment of the invention, a BBC such as TTR may be provided to an individual through gene therapy. To provide gene therapy to an individual, specific DNA sequences which code and express a desired protein are inserted into an appropriate vector complex which is then used to infect an individual in need of treatment. Various methods and vectors may be used for introducing a desired genetic sequence into an individual. The preferred and most often used method, incorporates the desired genetic sequence, for example a cDNA encoding TTR, into the genome of a retrovirus to form chimeric genetic material. The genetically altered retrovirus may then be used to infect the appropriate target cells in vitro or in vivo. Preferably, the retrovirus is altered so the desired sequences are inserted into the genome of the target host cells and replicated without replicating the infecting virus. The result of a successful gene transfer via a retrovirus vector is a virally infected host cell which expresses only the desired gene product. For reviews on gene therapy using retroviral vectors see WO 92/07943 published May 14, 1992 "Retroviral Vectors Useful for Gene Therapy" and Richard C. Mulligan, "Gene Transfer and Gene Therapy: Principle, Prospects and Perspective" in *Etiology of Human Disease at the DNA Level*, Chapter 12. Jan Linsten and Alf Peterson, eds. Rover Press, 1991, which are incorporated herein by reference. Additional viral vectors suitable for providing gene sequences include but are not limited to adeno-associated viruses, Herpes Simplex 1 Virus and vaccinia.

The biological activity of βAP has been demonstrated in a number of experiments (1, 16). Binding of TTR and other proteins to βAP may regulate its biological activity and play a role in the transport of the peptide.

The identification of βAP binding proteins suggests that prevention of βAP aggregation and amyloid formation requires a dynamic equilibrium of multiple extracellular factors participating in the sequestration of βAP. A decreased level of TTR in CSF (H. Riisoen, *Acta Neurol. Scand.* 78, 455 (1988); I. Elovaara, C. P. J. Maury, J. Palo, *Acta Neurol. Scand.* 74, 245 (1986)) and an increased expression of apoE, apoJ, and APP in the brains of AD patients (J. F. Diedrich et al., *J. Virol.* 65, 4759 (1991); D. L. Price, D. R. Borchelt and S. S. Sisodia, *Proc. Natl. Acad. Sci. U.S.A.* 90, 6381 (1993)). P. C. May et al., *Neuron* 5, 831 (1990) could alter the existing equilibrium and facilitate amyloid formation. Subtle differences, such as the single amino-acid substitution previously demonstrated for two apoE isoforms, may significantly influence the amount of amyloid formed in AD brains (D. E. Schmechel et al., *Proc. Natl. Acad. Sci. U.S.A.* (1993), 90:9649–9653). Over thirty mutations have been documented in TTR, and some lead to TTR amyloid formation in familial amyloidotic polyneuropathy (M. D. Benson and M. R. Wallace in *The Metabolic Basis of Inherited Disease*, C. R. Scriver, A. L. Beudet, W. S. Sly and D. Valle Eds. (McGraw-Hill Book Co., New York, 1989), pp. 2439–2460; D. R. Jacobson and J. N. Buxbaum in *Advances in Human Genetics* Vol. 20, H. Harris and K. Hirschhorn Eds. (Plenum Press, New York, 1991), pp. 69–123). Variants of TTR could be associated with AD in families not linked to other defined genetic loci on chromosomes 14, 19 and 21 (D. J. Selkoe, *Neuron* 6, 487 (1991); D. L. Price, D. R. Borchelt and S. S. Sisodia, *Prox. Natl. Acad. Sci. U.S.A.* 90, 6381 (1993); E. M. Castano and B. Frangione, *Lab. Invest.* 58, 122 (1988)) or modulate the effect of the defined loci. The suggested structure of TTR-βAP complex, furthermore, provides a molecular basis for the design of drugs to prevent amyloid formation.

EXAMPLES

Examle 1

A. To identify the proteins interacting with βAP in human CSF, synthetic $\beta API_{1-28}$ and $\beta AP_{1-40}$ labeled by an iodinated Bolton-Hunter reagent were used.

Synthetic $\beta AP_{1-28}$ and $\beta API_{1-40}$ from Bachem were radioiodinated using $^{125}I$ Bolton-Hunter reagent from Amersham according to manufacturer's instructions. Ten microliters of human CSF were incubated with $10^5$ dpm $^{125}I$-$\beta AP_{1-28}$ (specific activity $3-6\times10^6$ dpm/μg) in a final volume 20 μl PBS, pH 7.4 at 37° C. hours. Incubation under five (5) different conditions (A, B, C, D and E) were conducted to analyze complex formation of βAP. The incubation conditions were as follows:

(A) $^{125}I$-$\beta AP_{1-28}$ was incubated for 24 hours in PBS (FIG. 2(a), lane 1). $^{125}I$-$\beta AP_{1-28}$ was incubated for 24 hours in PBS, centrifuged through 20% sucrose cushion at 15000×g for 10 minutes and the pellet was analyzed by SDS-PAGE (FIG. 2(a), lane 2).

(B) Complexes of $^{125}I$-$\beta AP_{128}$ with CSF proteins formed after incubation for 24 hours (FIG. 2(b), lane 1) or 10 minutes (FIG. 2(b), lane 2). Complexes of $^{125}I$-$\beta AP_{1-28}$ with human apoE3 formed after incubation for 24 hours (FIG. 2(b), lane 3).

(C) Competition of complex formation of $^{125}$I-βAP$_{1-28}$ with CSF proteins by unlabeled βAP$_{1-28}$. Radiolabeled βAP was incubated with CSF (FIG. 1(d), lane 1), with CSF and 10 fold excess of unlabeled βAP$_{1-28}$ (FIG. 1(d), lane 2), with CSF and 200 fold excess of unlabeled βAP$_{1-28}$. A triangle indicates a 30 kDa band.

(D) Competition of complex formation of $^{125}$I-βAP$_{1-28}$ with TTR (Calbiochem) by unlabeled βAP$_{1-40}$. Radiolabeled βAP was incubated with 0.1 μM TTR (FIG. 1(f), lane 1), 0.1 μM TTR and 100 fold excess of unlabeled βAP-$_{1-40}$ (lane 2), 0.1 μM TTR and 500 fold excess of unlabeled βAP$_{1-40}$ (lane 3).

(E) Effect of boiling in SDS under reducing conditions on TTR-βAP complexes. $^{125}$I-βAP$_{1-28}$ was incubated with 0.1 μM TTR and before electrophoresis was incubated in 50 mM tris-HCL, pH 6.8 for 5 minutes at room temperature (FIG. 1, lane 1), or was boiled for 10 minutes in 50 mM tris-HCL, pH 6.8, 12% SDS and 0.2M β-mercaptoethanol (FIG. 1(g), lane 2).

Samples were mixed 1:1 with 2× loading buffer 100 mM tris-HCl, pH 6.8 and analyzed by 13% tris-tricine SDS-PAGE (A) or by 12% tris-glycine SDS-PAGE (B, C, D, E). The gels were dried and exposed to an X-ray X-Omat film from Kodak.

Time course experiments of complex formation demonstrated rapid formation of TTR-βAP complexes (FIGS. 1b and c) even in the presence of ApoE3 (FIG. 1(c)).

The experiments were repeated with $^{125}$I-βAP$_{1-28}$, and the same results were obtained.

When radiolabeled βAP$_{1-28}$ or βAP$_{1-40}$ was added to CSF samples, instead of aggregates, two bands with apparent molecular weights of 30 and 50 kDa were observed (FIG. 1b). These bands were distinct from the 40 kDa apoE-βAP complexes (FIG. 1b, lane 3) that were previously described (W. J. Strittmatter et al., Proc. Natl. Acad. Sci. U.S.A. 90, 8098 (1993); J. Ghiso et al., Biochem. J. 293, 27 (1993); W. J. Strittmatter et al., Experimental Neurology 122, 327 (1993)). The formation of radiolabeled βAP complexes in CSF could be specifically competed with unlabeled βAP (FIG. 1(d), lane 3.

B. The CSF protein that formed a 30 kDa complex with βAP was purified, subjected to trypsin digestion, and the two largest peptides were sequenced.

The purification of βAP binding activity was monitored using $^{125}$I-βAP$_{1-28}$ and SDS-PAGE and included three steps. Step 1: Chromatography of 5 ml CSF on a DEAE column and elution with a step-gradient in 50 mM tris-HCL, pH 7.4. The peak of binding activity was eluted at 0.4M NaCl. Step 2: The peak fractions were combined, diluted five times and further passed through a heparin-sepharose column in 50 mM NaCl, 50 Mm tris-HCl pH 7.4. The βAP binding activity appeared in unbound fractions. Step 3: The combined fractions containing βAP binding activity were chromatographed on a FPLC-mono Q column with a gradient 0.1–0.3M NaCl in 50 mM tris-HCl, pH 7.4. Fractions with peak activity from several experiments were combined, and 200 μg of purified protein were concentrated on a Speed Vac concentrator, reduced and alkylated. The protein was digested with trypsin and separated by reverse phase HPLC. The two largest peptides were sequenced by automated Edman degradation with an Applied Biosystems 477A sequencer with online PTH analysis using an Applied Biosystems 120A HPLC. The result of sequence analysis identified the sequences as ALGISPFHEHAEVVFTANDSGP and (SEQ ID NO:7) RYTIAALLSPYSYSTTAVVTNPK (SEQ ID NO:8).

C. The identified amino acid sequences of the two largest peptide sequences perfectly matched amino-acid residues 81 to 102 and 104 to 127, respectively, of transthyretin (TTR), a transporter of thyroxine and vitamin A in the brain (M. D. Benson and M. R. Wallace in The Metabolic Basis of Inherited Disease, C. R. Scriver, A. L. Beudet, W. S. Sly and D. Valle Eds. (McGraw-Hill Book Co., New York, 1989), pp. 2439–2460; D. R. Jacobson and J. N. Buxbaum in Advances in Human Genetics Vol. 20, H. Harris and K. Hirschhorn Eds. (Plenum Press, New York, 1991), pp. 69–123)). Commercial human plasma TTR also formed 30 kDa complexes with βAP$_{1-28}$ that could be competed with unlabeled βAP$_{1-40}$ demonstrating specificity of binding (FIG. 1(f), lane 3. TTR is a homotetrameric protein with 127 amino-acid residues in each chain, which dissociates to form 30 kDa dimers in SDS, and 15 kDa monomers after boiling in SDS with reducing agents (R. Murrell et al., J. Biol. Chem. 267 16595 (1992)). The 30 kDa TTR-βAP complexes appeared as 15 kDa complexes after boiling in SDS with reducing agents, suggesting that TTR monomer binds βAP (FIG. 1(g)). Using similar analytical techniques, we identified the CSF protein that formed the 50 kDa complex with radiolabeled βAP as albumin.

Example 2

We determined that TTR is the major βAP binding protein in CSF. Unlabeled βAP was incubated with CSF, TTR or bovine serum albumin, and the complexes were analyzed using Western blot techniques with anti-TTR and anti-βAP antibodies. Ten microgram of βAP$_{1-40}$ was incubated in 40 μl samples overnight at 37° C. in PBS, pH 7.2 with either 10μ CSF (FIG. 3(a), lane 1), 1 μg TTR (lane 2), or 50 μg BSA (lane 3). Controls consisted of ten microliters CSF (lane 4) or one microgram TTR (lane 5) in 40 μl PBS, pH 7.2 without βAP. The samples were analyzed by SDS-PAGE and immunoblotting using rabbit anti-βAP antibody SGY2134 kindly provided by Steven G. Younkin from Case Western Reserve University, Cleveland, Ohio. The same results were obtained with βAPI$_{1-28}$.

Ten microgram βAP$_{1-28}$ and 10 μl CSF were incubated in a 40 μl PBS, pH 7.2 overnight at 37° C. The sample was analyzed by SDS-PAGE and immunoblotting. (FIG. 3(b)). The membrane was cut lengthwise in two strips. One strip was immunostained with rabbit anti-βAP antibody SGY2134 (lane 1); the other strip was immunostained with sheep anti-TTR antibody, ICN Biochemicals, Inc. (lane 2). Immunoreactive proteins were detected by ECL method (Amersham). The same results were obtained with βAP$_{1-40}$.

Only TTR-βAP complexes with an apparent molecular weight of 30 kDa under non-reducing conditions were observed (FIG. 3). Complexes of βAP with purified albumin or with albumin in CSF were not detected. Thus, radioiodination of βAP by Bolton-Hunter reagent may cause the nonspecific binding of radiolabeled peptide to albumin.

Example 3

The effect of βAP binding proteins on aggregation of unlabeled βAP$_{1-28}$ was tested by a quantitative thioflavin-T fluorometric assay (H. LeVine III. Protein Science 2, 404 (1993). TTR was purchased from Calbiochem; bovine serum albumin, fraction V, was from Sigma; human serum apoE3 and apoE4 were isolated from human plasma as described by S. C. Rall, Jr., K. H. Weisgraber, R. W. Mahley, Methods Enzymol., 128, 273 (1986)). It has been suggested that apoE may promote amyloid formation (T. Wisniewski, A. Golabek, E. Matsubara, J. Ghiso, and B. Frangione, Biochem. Biophys. Res. Commun. 192, 359 (1993). Therefore, in addition to TTR, two isoforms of apoE and albumin were tested. (FIG. 4). The effect of different concentrations of bovine serum albumin (crosses), TTR (squares), ApoE3 (triangles), and apoE4 (circles) on βAP$_{1-28}$ aggregation was determined using an thioflavin T based fluorometric assay.

One hundred percent aggregation equals the average fluorescence signal of βAP. Synthetic $\beta AP_{1-28}$, at 300 µM in water was mixed with the indicated concentrations of BSA, TTR, apoE3, or ApoE4 and aggregation was initiated with 100 mM sodium acetate, pH 5.2. After 18 hours, 5 µsamples were mixed with 10 µM Thioflavin-T in 50 MM $KPO_4$ and the fluorescence was measured in arbitrary units at 450 nm excitation and 482 nm emission on a Perkin-Elmer LS-50 Fluorimeter (H. LeVine III. *Protein Science* 2, 404 (1993). TTR was purchased from Calbiochem; bovine serum albumin, fraction V, was from Sigma; human serum apoE3 and apoE4 were isolated from human plasma as described by S. C. Rall, Jr., K. H. Weisgraber, R. W. Mahley, *Methods Enzymol.*, 128, 273 (1986)).

Transthyretin, apoE3 and apoE4 reduced the fluorescence signal, indicating the prevention of synthetic $\beta AP_{1-28}$ aggregation, while albumin had no effect (FIG. 4). Inhibition of $\beta AP_{1-28}$ aggregation was dose dependent with a 50% reduction in signal observed at 1.4 µM for TTR and 0.4 µM for apoE3 or apoE4.

When amyloid found in patient tissues or aggregated synthetic βAP is stained with congo red, it produces a specific green to yellow birefringence when viewed under polarized light (D. J. Selkoe, *Neuron* 6, 487 (1991); D. L. Price, D. R. Borchelt and S. S. Sisodia, *Proc. Natl. Acad. Sci. U.S.A.* 90, 6381 (1993). Congo red staining of $\beta AP_{1-28}$ aggregates in the presence of 5 µM BSA (right panel) or 3 µM TTR (left panel) was therefore determined. FIG. 5. Synthetic $\beta AP_{1-28}$ at 300 µM was mixed with 5 µM BSA (left panel) or 3 µM TTR (FIG. 5, right panel) and aggregation was initiated with 100 mM sodium acetate, pH 5.2. After 18 hours, samples were mixed with 0.2% Congo red in 100 mM sodium acetate, pH 5.2 and 5 µl was spotted onto a microscope slide.

We found that the addition of albumin prior to aggregation of $\beta AP_{1-28}$ did not prevent the appearance of birefringence (FIG. 5, right panel). In contrast, when TTR or apoE was added to $\beta AP_{1-28}$ prior to aggregation, fewer or no characteristic aggregates producing birefringence were observed (FIG. 5, left panel).

Another feature of amyloid is the formation of fibrils with a characteristic electron microscopic pattern (D. J. Selkoe, *Neuron* 6, *487* (1991); D. L. Price, D. R. Borchelt and S. S. Sisodia, *Proc. Natl. Acad. Sci. U.S.A.* 90, 6381 (1993); E. M. Castano et al., *Biochem. Biophys. Res. Commun.* 141, 782 (1986); D. Burdick et al., *J. Biol. Chem.* 267, 546 (1992); J. T. Jarrett and P. T. Lansbury, Jr., *Cell, 73, 1055* (1993)). Synthetic $\beta AP_{1-28}$ readily forms these typical 5–10 nm thick amyloid fibrils (FIG. 6, right panel). $\beta AP_{1-28}$ aggregates without (right panel) or with 2 µM TTR (left panel) were analyzed using electron microscopy. One hundred microgram of $\beta AP_{1-28}$ was dissolved in water at concentration 100 µg/ml, sonicated for 15 seconds, added to 2 µM TTR, incubated for 16 hours at 37° C. in PBS pH 7.2, and stained with 2% uranyl acetate. Samples were examined and photographed at magnification of 25,000 on a Hitachi-12 electron microscope.

When βAP was incubated with TTR, only amorphous masses with few abortive short fibrils were observed, suggesting that TTR prevented formation of characteristic fibrils (FIG. 6, left panel). ApoE3 or apoE4 had the same effect as TTR (data not shown).

Example 4

In order to define the binding sites of βAP and TTR we built three dimensional molecular models of the TTR-βAP complex on computers. The molecular and solvent accessible surfaces of βAP and TTR were generated and electrostatic potentials were calculated using the Poisson-Boltzmann equation. We conducted these modellings on a Silicon Graphics Iris, 220 GTX. Coordinates for $\beta AP_{1-28}$ correspond to the solution structure as determined by 2D-NMR and distance geometry/simulated annealing (J. Talafous, K. J. Marcinowski, G. Klopman and M. G. Zagorski, manuscript submitted for publication). Coordinates for the structure of TTR had been determined by X-ray crystallography (C. C. F. Blake, M. J. Geisow, and S. J. Oatley, *J. Mol. Biol.* 121, 339 (1978)). It is strikingly clear that the electrostatic potentials of the alpha helical $\beta AP_{1-28}$ are very dipolar in nature (FIG. 7, top panel). Likewise, TTR has clearly demarcated regions that spawn negative (purple) or positive (yellow) electrostatic potentials (FIG. 7, center panel). The binding sites on βAP and TTR which would give the best fit between βAP and TTR were determined using the following constraints: (1) maximize surface contacts; (2) maintain the relative orientations to enhance electrostatic attraction; (3) bind the amyloid peptide to each subunit of TTR independently; and (4) avoid the TTR monomer surface involved in tetramer formation. Using these constraints we identified the binding scheme which is shown in FIG. 7, bottom panel, with TTR subunits colored blue and green and two $\beta AP_{1-28}$ molecules colored yellow.

Top (βAP) and center (TTR dimer) panels represent molecular surfaces shown in white and calculated electrostatic potentials shown as surface contours. The −1 kT potential contour is shown in purple and the +1 kT potential contour is shown in yellow. Bottom panel represent TTR-$\beta AP_{1-28}$ complex as a space filling model. For clarity monomers of TTR dimer are shown in blue and green. Two βAP molecules are shown in yellow (19).

The following amino-acid residues were found on the contacting surface of βAP: Arg (5), Ser (8), Gly (9), Val (12), His (13), Gln (15), Lys (16), Phe (19), Phe (20), Asp (23), Val (24), Asn (27), Lys (28).

In addition, the following amino-acid residues were found on the contacting surface of TTR dimer: Arg (34, 161), Ala (37, 164), Asp (38, 165), Thr (40, 167), Glu (42, 169), Glu (62, 189), Val (65, 192), Glu (66, 193). The first number in parenthesis is the residue number for the first subunit and the second number for the second subunit of TTR.

While not wishing to be bound by theory, we believe that the specific contribution of the amino acids on the TTR surface which binds specifically to the βAP peptide is twofold. First, they provide the building blocks for the detailed shape of the surface. Second, they provide the charge that engenders a positive electrostatic potential which covers the whole surface with a value of +1 kT (at T=298° K., k is the Boltzmann constant) at approximately 2 to 5 Å from the solvent accessible surface. A concave, positive potential inducing surface of $\beta AP_{1-28}$ containing the residues Arg (5), His (13), Lys (16) and Lys (28) was identified which matches remarkably well with the convex negative potential inducing surface on TTR containing the residues Asp (38, 165), Glu (42, 169), Glu (62, 189), and Glu (66, 193).

Our experiments clearly show that sequestered βAP cannot participate in amyloid fibril formation. While TTR is not the only protein that binds βAP (W. J. Strittmatter et al., *Proc. Natl. Acad. Sci. U.S.A.* 90, 8098 (1993); J. Ghiso et al., *Biochem. J.* 293, 27 (1993); W. J. Strittmatter et al., *Experimental Neurology* 122, 327 (1993)), it is the major βAP sequestering protein in human CSF. The concentration of TTR is two orders of magnitude greater than concentration of βAP and is higher than the concentration of other known βAP binding proteins in CSF. The approximate concentrations are 3 nM for βAP, 2 µM for albumin, 0.3 µM for TTR, 0.1 µM for apoE, 0.03 µM for apoJ, and 0.03 µM for APP (P. Seubert et al., *Nature* 359, 325 (1992); M. Shoji et al., *Science* 258, 126 (1992); B. A. Yankner, L. K. Duffy and D.

A. Kirschner, *Science* 250, 279 (1990); D. M. Araujo and C. W. Cotman, *Brain Res.* 569, 141 (1992); M. P. Matson, et al., *J. Neurosci.* 12, 376 (1992); C. Behl, J. Davis, G. M. Cole and D. Schubert, *Biochem. Biophys. Res. Commun.* 186, 944 (1992)). Our data do not exclude the possibility that other proteins form complexes with βAP; however, most, if not all, βAP is probably sequestered by TTR (FIGS. 1 and 3).

Example 5

Identification of TTR mutation.

Genetic linkage studies have reported several loci for familial AD (FAD) on chromosomes 21, 14, 19. However many FAD pedigrees have not shown evidence for linkage to these chromosomes, suggesting a genetically heterogeneous mechanism of disorder and existence of additional FAD susceptible genes.

Because of TTR's importance in amyloid formation, the TTR gene could be a candidate for FAD and sporadic AD in families not linked to defined genetic loci on chromosomes 14, 19 and 21 or modulate effect of defined loci.

In order to identify a mutation in the TTR gene associated with AD, we have analyzed by PCR-Single Strand Conformation Polymorphism (SSCP), the sequence of three TTR exons in 55 unrelated AD patients.

PCR-SSCP analysis was performed according to the method of Orita et al. (Orita M, Suzuki Y, Sekiya T., Hayashi K., Genomics 5:874–879). In all cases, one 5' end-labeled primer and one unlabeled primer were used for genomic PCR amplification. Oligonucleotides for all exons are listed in Table 1.

TABLE 1

| Exon | Oligonucleotide | Position |
|------|-----------------|----------|
| 2 | 5'CGC TCC AGA TTT CTA ATA CCAC 3' | 1515–1537 (SEQ ID NO: 1) |
|   | 5'AGT GAG GGG CAA ACG GGA AGAT 3' | 1791–1769 (SEQ ID NO: 2) |
| 3 | 5'TGG TGG GGG TGT ATT ACT TTGC 3' | 3446–3468 (SEQ ID NO: 3) |
|   | 5'CAT TTC CTG GAA TGC CAA AAGC 3' | 4022–4000 (SEQ ID NO: 4) |
| 4 | 5'GGT CAG TCA TGT TGT TCA TCTG 3' | 7193–7215 (SEQ ID NO: 5) |
|   | 5'TAG TAA AAA TGG AAT ACT CTTG 3' | 7447–7425 (SEQ ID NO: 6) |

Primers were 5' end labeled with 32p-ATP using T4 polynucleotide kinase according to manufacturers instructions (New England BioLabs). The PCR mixture contained 12.5 ng of both primers, 5 nmol of dNTP, 250 ng of genomic DNA and 1.25 U of AmpliTag polymerase (Perkin-Elmer Cetus). PCR was performed in a Perkin Elmer-Cetus DNA thermal cycler for 30 cycles (each cycle was 94 C-1 min, 56 C-1 min, 72 C-2 min, Extension 72-10 min. Electrophoresis was carried out at 4 C in 6% polyacrylamide gel.

PCR-SCCP revealed a polymorphism in exon 2 in 7 patients with AD. The amplified sequence of exon 2 was cloned in the pCR™ vector (Invitrogen) and target DNA was sequenced using a DNA Sequencing KIT (USB).

Ten (10) patients had a heterozygous G-A substitution in codon 6, which changed the normal glycine codon, GGT, to one for serin, AGT. This TTR variant originally was described as a variant with elevated thyroxine-binding affinity (Fitch N. J. S. et al., Journal of Endocrinology, 1991, 129, 309–313.). Although the gene frequency of the serine 6 TTR variant was found to be 12% in North American Caucasians (Jacobsen et al. supra.), we have found that the frequency of this variant in our random selected population of AD patients increased up to 18%.

G-A substitution in serine 6 variant of TTR creates a BsrI site. This enzyme might therefore be used for RFLP analysis of the TTR gene in AD pedigrees. Using the same conditions and the same primers for exon 2 (Table 1), we analyzed the PCR product for the presence of the BsrI restriction site (FIG. 8). These data show that the serine 6 TTR variant, as well as other TTR variants, could be associated with AD and can provide a genetic diagnostic test for some forms of AD.

While we have hereinbefore described a number of embodiments of this invention, it is apparent that the basic constructions can be altered to provide other embodiments which utilize the methods of this invention.

Therefore, it will be appreciated that the scope of this invention is defined by the claims appended hereto rather than by the specific embodiments which have been presented hereinbefore by way of example.

We claim:

1. An in vitro method to detect the ability of a soluble transthyretin (TTR) present in a sample, to specifically bind soluble amyloid β protein (βAP), said method comprising:

(a) contacting the sample containing the soluble TTR with βAP to form a transthyretin (TTR)/βAP complex, and;

(b) detecting said complex wherein the presence of said complex indicates the ability of the soluble TTR to specifically bind βAP.

2. The method according to claim 1 wherein the sample is CSF.

3. The method according to claim 1 wherein the βAP is bound to a solid support.

4. An in vitro method to detect the ability of a soluble transthyretin (TTR) present in a sample, to specifically bind a soluble amyloid β protein (βAP), said method comprising:

(a) forming a complex comprising a labelled TTR specifically bound to the βAP; and (b) contacting the sample suspected of containing soluble TTR with said complex; and (c) detecting the displacement of said labelled TTR from said complex wherein the displacement of said labelled TTR from said complex indicates the presence of soluble TTR in the sample.

5. The method according to claim 4 wherein said βAP is bound to a solid support.

6. An in vitro method to detect soluble amyloid β protein (βAP) in a sample, said method comprises:

(a) forming a complex comprising a labelled ligand specifically bound to a transthyretin (TTR); and (b) contacting the sample suspected of containing soluble βAP with said complex; and (c) detecting the displacement of said labelled ligand from said complex wherein the displacement of labelled ligand from the TTR indicates the presence of soluble βAP in the sample.

7. The method according to claim 6 wherein TTR is bound to a solid support and the labelled ligand is a predetermined amount of βAP.

8. An in vitro method to detect the ability of a soluble amyloid β-protein (βAP) present in a sample, to specifically bind a transthyretin (TTR), said method comprising:

(a) contacting the sample containing the βAP with the TTR to form a transthyretin (TTR)/βAP complex, and;

(b) detecting said complex wherein the presence of said complex indicates the ability of the soluble βAP to specifically bind TTR.

9. The method according to claim 8, wherein the TTR is bound to a solid support.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 22
        ( B ) TYPE: NUCLEOTIDE
        ( C ) STRANDEDNESS: SINGLE
        ( D ) TOPOLOGY: UNKNOWN ( x i ) SEQUENCE DESCRIPTION: SEQ ID NO:1:

CGCTCCAGAT TTCTAATACC AC        22

( 2 ) INFORMATION FOR SEQ ID NO:2:

( i ) SEQUENCE CHARACTERISTICS:
    ( A ) LENGTH: 22
    ( B ) TYPE: NUCLEOTIDE
    ( C ) STRANDEDNESS: SINGLE
    ( D ) TOPOLOGY: UNKNOWN ( x i ) SEQUENCE DESCRIPTION: SEQ ID NO:2:

AGTGAGGGGC AAACGGGAAG AT        22

( 2 ) INFORMATION FOR SEQ ID NO:3:

( i ) SEQUENCE CHARACTERISTICS:
        ( A ) LENGTH: 22
        ( B ) TYPE: NUCLEOTIDE
        ( C ) STRANDEDNESS: SINGLE
        ( D ) TOPOLOGY: UNKNOWN ( x i ) SEQUENCE DESCRIPTION: SEQ ID NO:3:

TGGTGGGGGT GTATTACTTT GC        22

( 2 ) INFORMATION FOR SEQ ID NO:4:

( i ) SEQUENCE CHARACTERISTICS:
        ( A ) LENGTH: 22
        ( B ) TYPE: NUCLEOTIDE
        ( C ) STRANDEDNESS: SINGLE
        ( D ) TOPOLOGY: UNKNOWN ( x i ) SEQUENCE DESCRIPTION: SEQ ID NO:4:

CATTTCCTGG AATGCCAAAA GC        22

( 2 ) INFORMATION FOR SEQ ID NO:5:

( i ) SEQUENCE CHARACTERISTICS:
        ( A ) LENGTH: 22
        ( B ) TYPE: NUCLEOTIDE
        ( C ) STRANDEDNESS: SINGLE
        ( D ) TOPOLOGY: UNKNOWN ( x i ) SEQUENCE DESCRIPTION: SEQ ID NO:5:

GGTCAGTCAT GTTGTTCATC TG        22

( 2 ) INFORMATION FOR SEQ ID NO:6:

( i ) SEQUENCE CHARACTERISTICS:
        ( A ) LENGTH: 22
        ( B ) TYPE: NUCLEOTIDE
        ( C ) STRANDEDNESS: SINGLE
        ( D ) TOPOLOGY: UNKNOWN ( x i ) SEQUENCE DESCRIPTION: SEQ ID NO:6:

TAGTAAAAAT GGAATACTCT TG        22

( 2 ) INFORMATION FOR SEQ ID NO:7:

( i ) SEQUENCE CHARACTERISTICS:
        ( A ) LENGTH: 22
        ( B ) TYPE: AMINO ACID
        ( C ) STRANDEDNESS: SINGLE
        ( D ) TOPOLOGY: UNKNOWN ( x i ) SEQUENCE DESCRIPTION: SEQ ID NO:7:

Ala Leu Gly Ile Ser Pro Phe His Glu His Ala Glu
1               5                   10

Val Val Phe Thr Ala Asn Asp Ser Gly Pro
        15                  20

( 2 ) INFORMATION FOR SEQ ID NO:8:

( i ) SEQUENCE CHARACTERISTICS:
        ( A ) LENGTH: 23
        ( B ) TYPE: AMINO ACID
        ( C ) STRANDEDNESS: SINGLE
        ( D ) TOPOLOGY: UNKNOWN ( x i ) SEQUENCE DESCRIPTION: SEQ ID NO:8:

```
Arg  Tyr  Thr  Ile  Ala  Ala  Leu  Leu  Ser  Pro  Tyr  Ser
 1               5                          10

Tyr  Ser  Thr  Thr  Ala  Val  Val  Thr  Asn  Pro  Lys
         15                    20
```